United States Patent
Lind et al.

(10) Patent No.: US 8,833,187 B2
(45) Date of Patent: Sep. 16, 2014

(54) STACK SAMPLING APPARATUS

(75) Inventors: Randall F. Lind, Knoxville, TN (US);
Peter D. Lloyd, Knoxville, TN (US);
Lonnie J. Love, Knoxville, TN (US);
Mark W. Noakes, Knoxville, TN (US);
Francois G. Pin, Knoxville, TN (US);
Bradley S. Richardson, Knoxville, TN (US); John C. Rowe, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 817 days.

(21) Appl. No.: 13/033,231

(22) Filed: Feb. 23, 2011

(65) Prior Publication Data

US 2012/0210805 A1    Aug. 23, 2012

(51) Int. Cl.
| | |
|---|---|
| *G01N 1/08* | (2006.01) |
| *G01T 7/02* | (2006.01) |
| *G12B 5/00* | (2006.01) |
| *E21B 49/06* | (2006.01) |
| *E21B 49/10* | (2006.01) |
| *G01N 1/10* | (2006.01) |

(52) U.S. Cl.
CPC .......... *G01N 1/08* (2013.01); *G01N 2001/1037* (2013.01); *G12B 5/00* (2013.01); *G01T 7/02* (2013.01); *E21B 49/06* (2013.01); *E21B 49/10* (2013.01)
USPC .................. 73/864.45; 73/863.31; 73/863.81; 73/866.5

(58) Field of Classification Search
CPC ......... G01D 11/00; G01D 11/30; G01N 1/08; G01N 2001/103; G01T 7/00; G01T 7/02
USPC .............. 73/863.31, 863.33, 863.81–863.82, 73/863.86, 864, 864.34, 864.41, 864.45
See application file for complete search history.

(56) References Cited

U.S. PATENT DOCUMENTS

| | | | | |
|---|---|---|---|---|
| 4,502,253 A | * | 3/1985 | Lorenzi et al. | 451/6 |
| 4,541,278 A | * | 9/1985 | Marsh et al. | 73/592 |
| 8,020,460 B1 | * | 9/2011 | Hoyt | 73/866.5 X |
| 2006/0230846 A1 | * | 10/2006 | Smith et al. | 73/866.5 |

FOREIGN PATENT DOCUMENTS

| | | | | | |
|---|---|---|---|---|---|
| EP | 237698 A2 | * | 9/1987 | | G12B 5/00 |
| EP | 411874 A2 | * | 2/1991 | | G01N 27/90 |
| EP | 538084 A1 | * | 4/1993 | | 324/664 |
| GB | 2267302 A | * | 12/1993 | | E01F 9/01 |
| GB | 2436618 A | * | 10/2007 | | G01B 11/12 |
| JP | 09229868 A | * | 9/1997 | | G01N 21/88 |
| NL | 9002000 A | * | 4/1992 | | G01N 1/08 |

OTHER PUBLICATIONS

Winterholler et al., "Automated Core Sample Handling for Future Mars Drill Missions," 8th International Symposium on Artificial Intelligence, Robotics and Automation in Space, Germany 2005, pp. 1-8.

* cited by examiner

*Primary Examiner* — Thomas P Noland
(74) *Attorney, Agent, or Firm* — Klarquist Sparkman, LLP

(57) ABSTRACT

An apparatus for obtaining samples from a structure includes a support member, at least one stabilizing member, and at least one moveable member. The stabilizing member has a first portion coupled to the support member and a second portion configured to engage with the structure to restrict relative movement between the support member and the structure. The stabilizing member is radially expandable from a first configuration where the second portion does not engage with a surface of the structure to a second configuration where the second portion engages with the surface of the structure.

15 Claims, 15 Drawing Sheets

STACK SAMPLING APPARATUS

ACKNOWLEDGMENT OF GOVERNMENT SUPPORT

This invention was made with government support under Contract No. DE-AC05-00OR22725 awarded by the U.S. Department of Energy. The government has certain rights in the invention.

FIELD

The present disclosure relates generally to devices and methods for collecting samples of materials for identification and/or analysis, and, more particularly, to remote sampling systems and methods.

BACKGROUND

Structures that have been, or may have been, exposed to contaminated materials must be inspected and analyzed to determine the extent, if any, of their contamination prior to taking any actions with respect to the structure. For example, remediation of off-gas ventilation stacks requires determining qualitative and quantitative levels of contamination inside each stack in order to determine the plan for demolition and waste disposal.

In many cases, the portions of these structures that have been potentially contaminated are difficult to access. For example, since the purpose of an off-gas stack is to disperse airborne contaminants into the atmosphere at acceptable levels, many of them are hundreds of feet high. Moreover, even if the areas from which samples are to be obtained are physically accessible, placing workers in full personal protective equipment into contaminated stacks of unknown structural integrity to collect the necessary characterization data can be undesirable.

SUMMARY

In one embodiment, an apparatus for providing remote access to a structure is provided. The apparatus includes a support member, at least one stabilizing member, and at least one moveable member. The stabilizing member has a first portion coupled to the support member and a second portion configured to engage with the structure to restrict relative movement between the support member and the structure. The stabilizing member is radially expandable from a first configuration where the second portion does not engage with a surface of the structure to a second configuration where the second portion engages with the surface of the structure. The moveable member has a first end and a second end, with the first end being coupled to the support member and the second end being coupled to an instrument. The moveable member can be configured to radially expand to move the instrument adjacent to a surface of the structure.

In some embodiments, three stabilizing members can extend from the support member, and the second portions of the contacting the surface of the structure in a generally triangular pattern. The three stabilizing members can each have a first arm member, a second arm member, and a link member pivotably coupling the first and second arm members. A base member can be coupled to the support member and the first end of the moveable member, with the base member being rotatable relative to the support member. The moveable member can have a first arm member, a second arm member, and a link member pivotably coupling the first and second arm members.

In other embodiments, the instrument can be carried by an instrument support coupled to the second end of the moveable member. The instrument support can carry one or more instruments. The instrument can be a core sampler that includes a plurality of core bits rotatably coupled to a turret and at least one driver configured to advance each of the core bits towards the surface of the structure and rotate the core bits to capture samples from the structure. The instrument can include a housing that substantially encloses the plurality of core bits, with the housing having at least one opening through which each core bit can be advanced toward the surface of the structure. A vacuum port can be positioned generally in line with the opening to remove debris from the vicinity of a rotating core bit. A wedge tool can also be provided, with the wedge tool having a ramped portion that is moveable at least partly into an interior area of the core bits after a sample has been captured.

In other embodiments, the instrument can include a plurality of extension members having a first end and a second end, with the second end of the extension members having a sampling surface. A housing can substantially enclose the plurality of extension members, with the housing having at least one opening through which each extension member can be advanced towards the surface of the structure. The sampling surfaces can be configured to contact the surface of the structure to obtain a sample of the surface of the structure.

There can be a single opening in the housing through which each of the extension members is advanced, and the plurality of extension members can be rotatable so that each extension member can be moved into alignment with the single opening. A shutter can be movable between a closed position where the shutter substantially blocks the single opening and an open position where the shutter does not block the single opening. A detent can be provided to allow at least a portion of the extension member to break off when a torque is applied to the extension member.

In other embodiments, the instrument can be a radiation detector. The radiation detector can include a radiation sensor and a motion-limiting member to position the radiation sensor a desired distance from the surface of the structure.

In another embodiment, a method of obtaining samples from an interior of a structure is provided. The method can include lowering an apparatus into an opening in a structure. The apparatus has a support member and at least one stabilizing member. The stabilizing members are radially expanded to engage with a surface of the structure to restrict relative movement between the support member and the structure. An instrument is moved radially outward toward the surface of the structure to position the instrument adjacent the surface of the structure. The instrument is activated to obtain a sample from the surface of the structure.

In some embodiments, three stabilizing members can extend from the support member. Radially expanding the stabilizing members comprises extending the stabilizing members to contact the surface of the structure in a generally triangular pattern. The three stabilizing members can each comprise a first arm member, a second arm member, and a link member. Radial expansion of the stabilizing members can include pivoting the first and second arm member about the link member.

In other embodiments, the apparatus comprises a base member that is coupled to the support member and the first end of the at least one moveable member. The base member can be rotated relative to the support member to adjust the position of the instrument relative to the structure. The instrument can be coupled to a moveable member that comprises a first arm member, a second arm member, and a link member between the first and second arm members. Moving the instrument radially outward includes pivoting the first and second arm members about the link member.

In other embodiments, the instrument can be carried by an instrument support coupled to an end of the moveable member. Moving the instrument radially outward towards the surface of the structure includes moving the instrument support towards the surface of the structure. The instrument can be a core sampler and the method can include advancing a core bit towards the surface of the structure and rotating the core bit to capture a sample from the structure, and withdrawing the core bit from the structure with the captured sample held in the interior of the core bit. A wedge tool can be advanced into the interior of the core bit to facilitate separation of the captured sample from the structure. A plurality of core bits can be provided and after the core bit is advanced and withdrawn through an opening in an instrument housing, a turret can be rotated to move the core bit with the captured sample to a position away from the opening and to move another core bit into alignment with the opening. A negative pressure can be created in the vicinity of the core bit to remove debris generated by the rotating core bit.

The instrument can also comprise a contact sampler. Activating the instrument to obtain a sample from the surface of the structure can include advancing an extension member with a sampling surface into contact with the surface of the structure to capture a sample from the structure and withdrawing the extension member and sampling surface with the captured sample thereon from contact with the surface of the structure. The instrument can include a plurality of contact samplers and after the extension member and sampling surface is advanced and withdrawn through an opening in an instrument housing, a carousel supporting the plurality of extension members and sampling surfaces can be rotated to move the extension member with the sampling surface that contains the captured sample thereon to a position away from the opening and to move another extension member and sampling surface into alignment with the opening. A shutter can open to allow the extension member with a sampling surface to advance through the opening. The shutter can close when an extension member with a sampling surface is not advanced through the opening. Each extension member can include a detent configured to allow at least a portion of the extension member to break off when a torque is applied to the extension member.

In other embodiments, the instrument can include a radiation detector. The radiation detector can have a radiation sensor and a motion-limiting member. The radiation sensor can be positioned a desired distance from the surface of the structure by moving the instrument support until the motion-limiting member restricts further movement of the radiation sensor.

In another embodiment, a method of obtaining samples from an interior of a structure using a remotely-operated apparatus is provided. The method can include placing the apparatus into an enclosure. The enclosure has a base and side walls that generally surround the apparatus. The base of the enclosure can be mounted on an opening into an interior of a structure and the apparatus can be lowered out of the enclosure and into the interior of the structure. The apparatus can be fixed relative to the structure by radially expanding three or more stabilizing members to engage with a surface of the interior of the structure. An instrument can be moved radially outward toward the surface of the structure to position the instrument adjacent the surface of the structure. The instrument can be activated to obtain a sample from the surface of the structure. The apparatus can be raised out of the opening and back into the enclosure and the enclosure and apparatus can be removed from the structure. The apparatus can be lowered into the opening and raised out of the opening by a crane.

The instrument can include a plurality of core samplers, with each core sampler having a core bit that can extend into the structure to capture a sample of the structure. The instrument can have at least six core samplers. The instrument can include a plurality of contact samples, with each contact sampler having a sampling surface that can extend into contact with a surface of the structure to capture a sample of the structure. The sampling surfaces can include an adhesive material to facilitate capture of the sample.

The foregoing and other objects, features, and advantages of the invention will become more apparent from the following detailed description, which proceeds with reference to the accompanying figures.

DETAILED DESCRIPTION

Various embodiments of sampling systems and their methods of use are disclosed herein. The following description is exemplary in nature and is not intended to limit the scope, applicability, or configuration of the invention in any way. Various changes to the described embodiments may be made in the function and arrangement of the elements described herein without departing from the scope of the invention.

As used in this application and in the claims, the singular forms "a," "an," and "the" include the plural forms unless the context clearly dictates otherwise. Additionally, the term "includes" means "comprises." Further, the term "coupled" generally means electrically, electromagnetically, and/or physically (e.g., mechanically or chemically) coupled or linked and does not exclude the presence of intermediate elements between the coupled or associated items absent specific contrary language.

Although the operations of exemplary embodiments of the disclosed method may be described in a particular, sequential order for convenient presentation, it should be understood that the disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Remote Access Characterization System

Remediation of structures that have been exposed to contamination, such as radiological and chemical contaminants, can require characterization of the structure to resolve waste disposition issues. Such structures can include, for example, off-gas ventilation stacks that are difficult to physically access and/or inspect to access due to the height of the structure, questions regarding the integrity of the structure, and/or the size of the space or openings associated with the structure. To further complicate matters, stack height, top and bottom inside diameters, and the methods of construction of such structures can vary widely.

Figure 1:
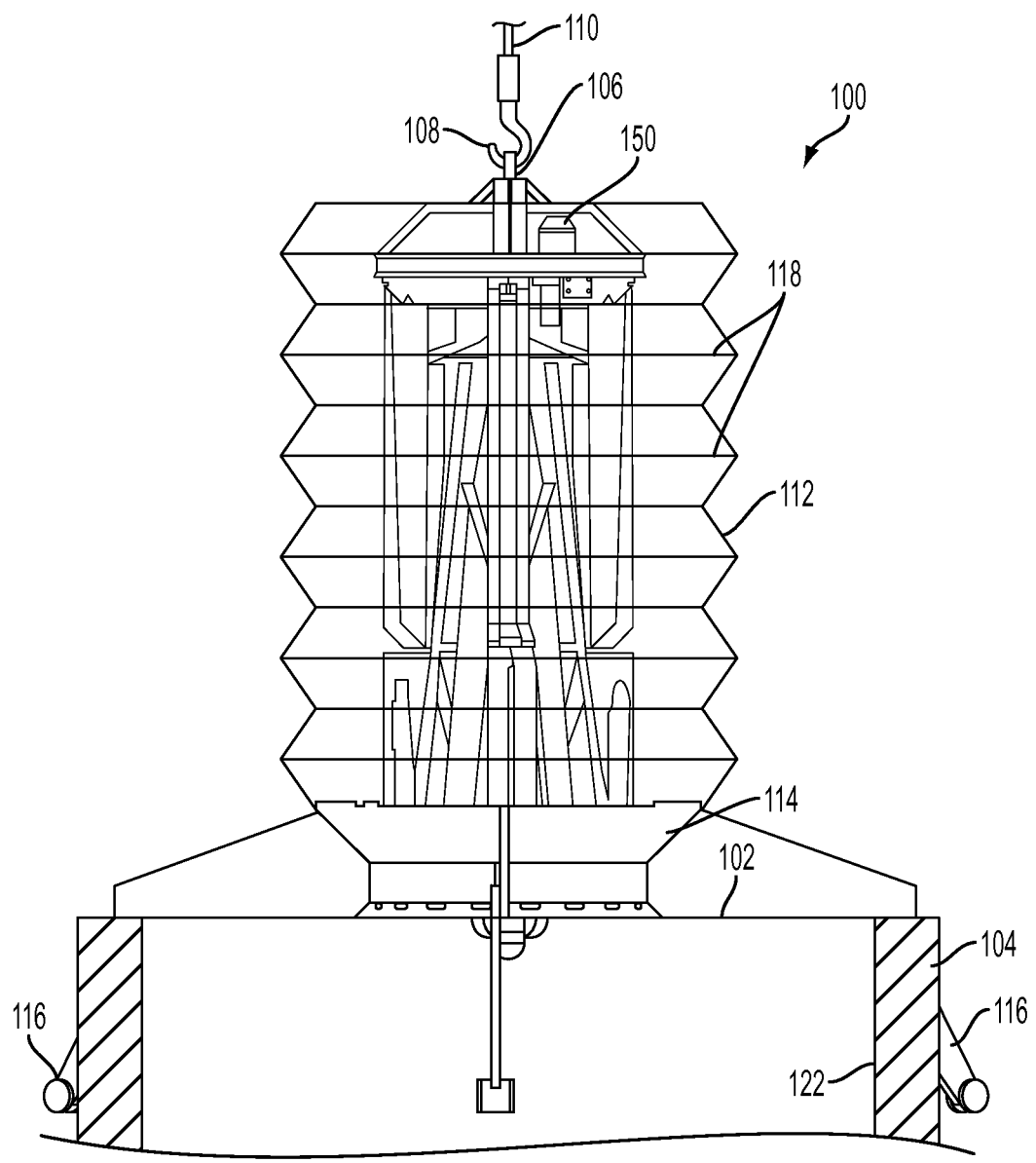
FIG. 1 illustrates a side view of an apparatus capable of providing remote access to a structure, such as the inside of an off-gas ventilation stack.

FIG. 1 illustrates an apparatus 100 capable of providing access to a confined space, such as the inside of an off-gas ventilation stack. Although the following methods and systems are generally shown and described in the context of providing remote access to off-gas ventilations stacks, it should be understood that these methods and systems can also be used to remotely access and inspect various areas of other structures.

FIG. 1 is a partial cross-sectional view showing apparatus 100 being delivered into an opening 102 in a structure 104. As noted above, structure 102 can comprise an off-gas ventilation stack and opening 102 can comprise the top stack opening. Apparatus 100 can have a loop, ring, or other similar structure 106 to receive a hook 108 coupled to a cable 110. Cable 110 can be, for example, a crane cable that can lower and raise apparatus 100 into and out of structure 104. As described in more detail below, once lowered into structure 104, apparatus 100 can inspect, analyze, and/or obtain one or more samples from the structure for off-site analysis.

An enclosure 112 can be provided to generally surround opening 102. Enclosure 112 can comprise a containment cap 114 that generally rests on and/or covers a portion of opening 102. A plurality of legs 116 can extend from containment cap 114 to hold enclosure 112 in position at the opening 102 of structure 104. Because the size of openings 102 and/or top portions of structures 104 can vary, legs 116 can be flexible or otherwise adjustable to accommodate various size structures 104.

Enclosure 112 can comprise a rigid or collapsible structure. If formed as a collapsible structure, enclosure 112 is preferably able to collapse under its own weight. By allowing enclosure 112 to collapse as apparatus 100 is lowered into structure 104, the effects of wind and other environmental conditions on enclosure 112 can be reduced. Thus, for example, enclosure 112 can comprise a collapsible non-rigid material such as clear polyurethane film. If additional rigidity or weight is desired to cause enclosure 112 to collapse when apparatus 100 is lowered into opening 102, one or more ring elements 118 can be provided, thereby forming an accordion-type, or bellows-type structure. Enclosure 112 can generally surround apparatus 100 to reduce the risk that contamination captured or otherwise stirred up by apparatus 100 will be spread or disseminated outside of structure 104 as apparatus 100 is removed from structure 104.

Figure 2:
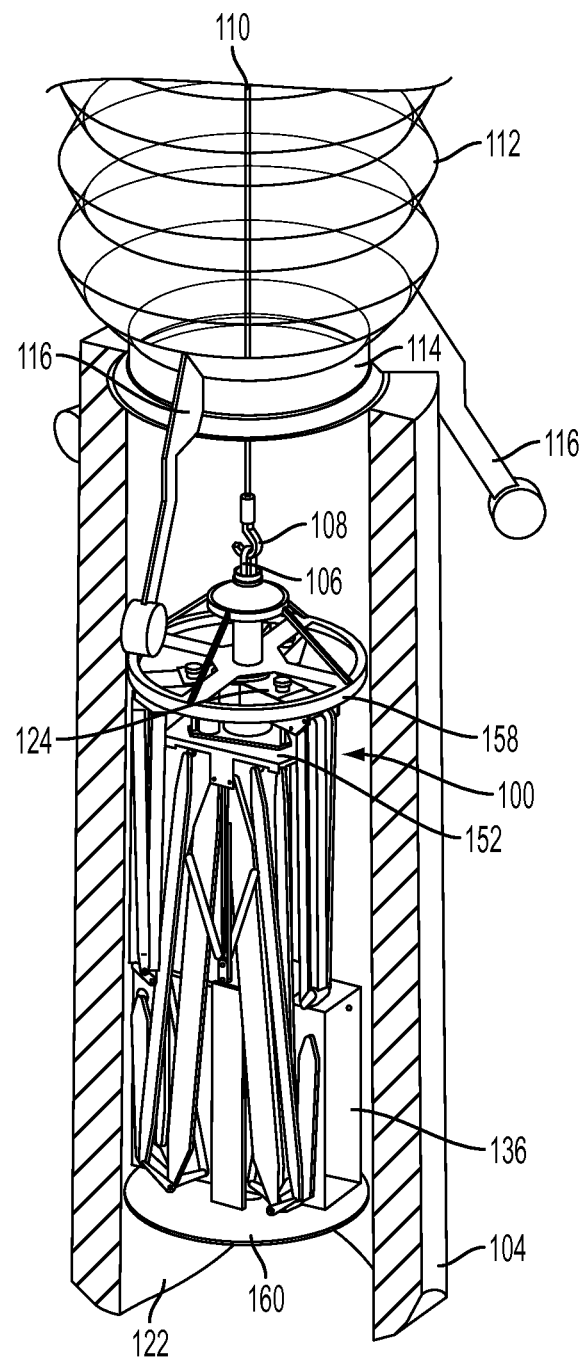
FIG. 2 illustrates a view of an apparatus capable of providing remote access to a structure, shown in a collapsed configuration and being lowered into an off-gas ventilation stack.
Figure 3:
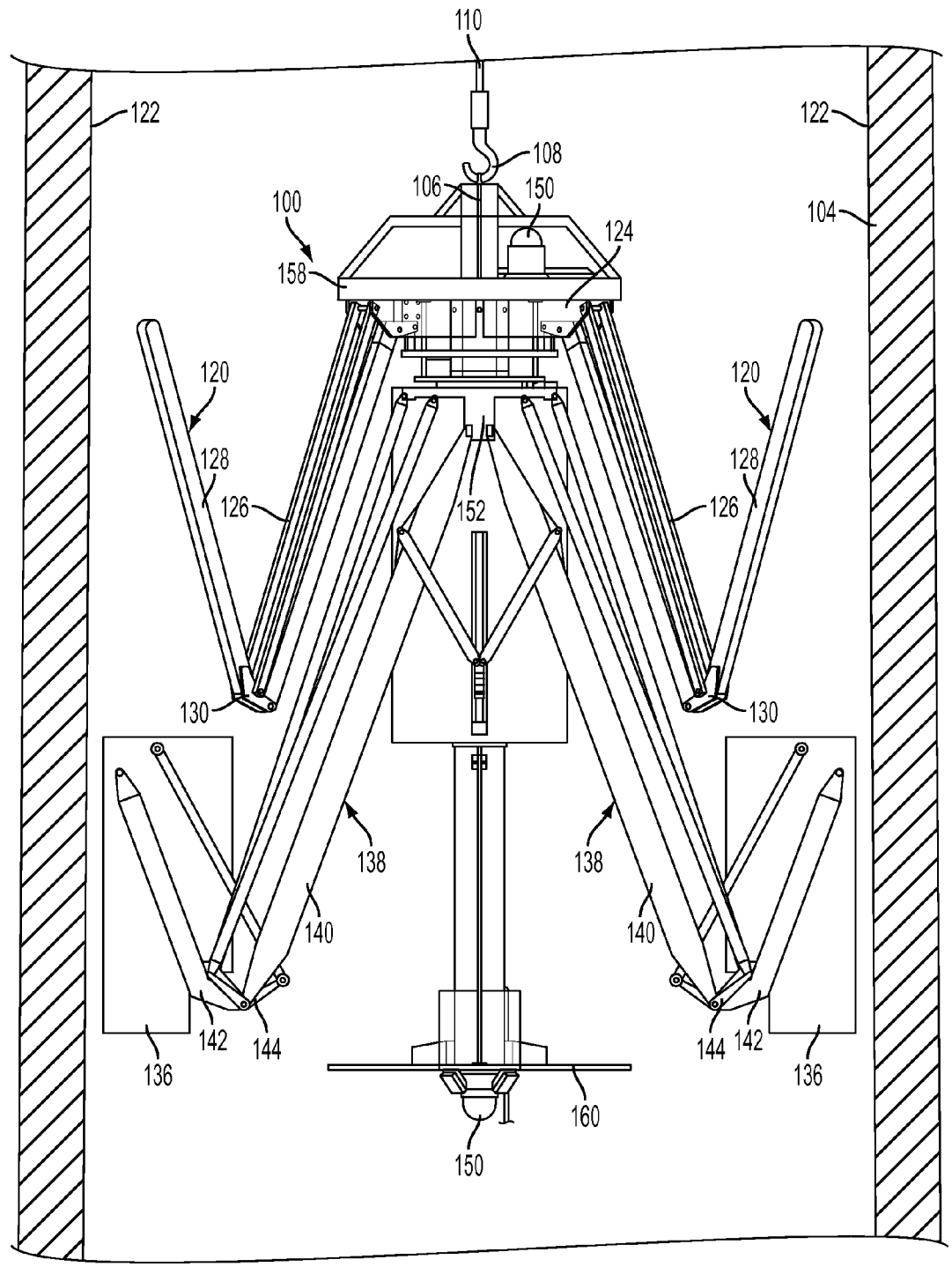
FIG. 3 illustrates a view of an apparatus capable of providing remote access to a structure, shown in an expanded configuration within an off-gas ventilation stack.

Referring to FIGS. 2 and 3, apparatus 100 is depicted being lowered into structure 104 by cable 110. Apparatus 100 is moveable between a collapsed configuration (FIG. 2) and an expanded configuration (FIG. 3). Apparatus 100 has a relatively small profile (e.g., diameter) in the collapsed configuration and a significantly larger profile (e.g., diameter) in the expanded configuration. Many structures have widths that vary along the height of the structure. For example, most off-gas ventilation stacks have a narrower opening at the top than at the bottom. As shown in FIG. 2, the ability to move into a collapsed configuration permits apparatus 100 to be able to be delivered through narrow passageways, such as opening 102.

Figure 5:
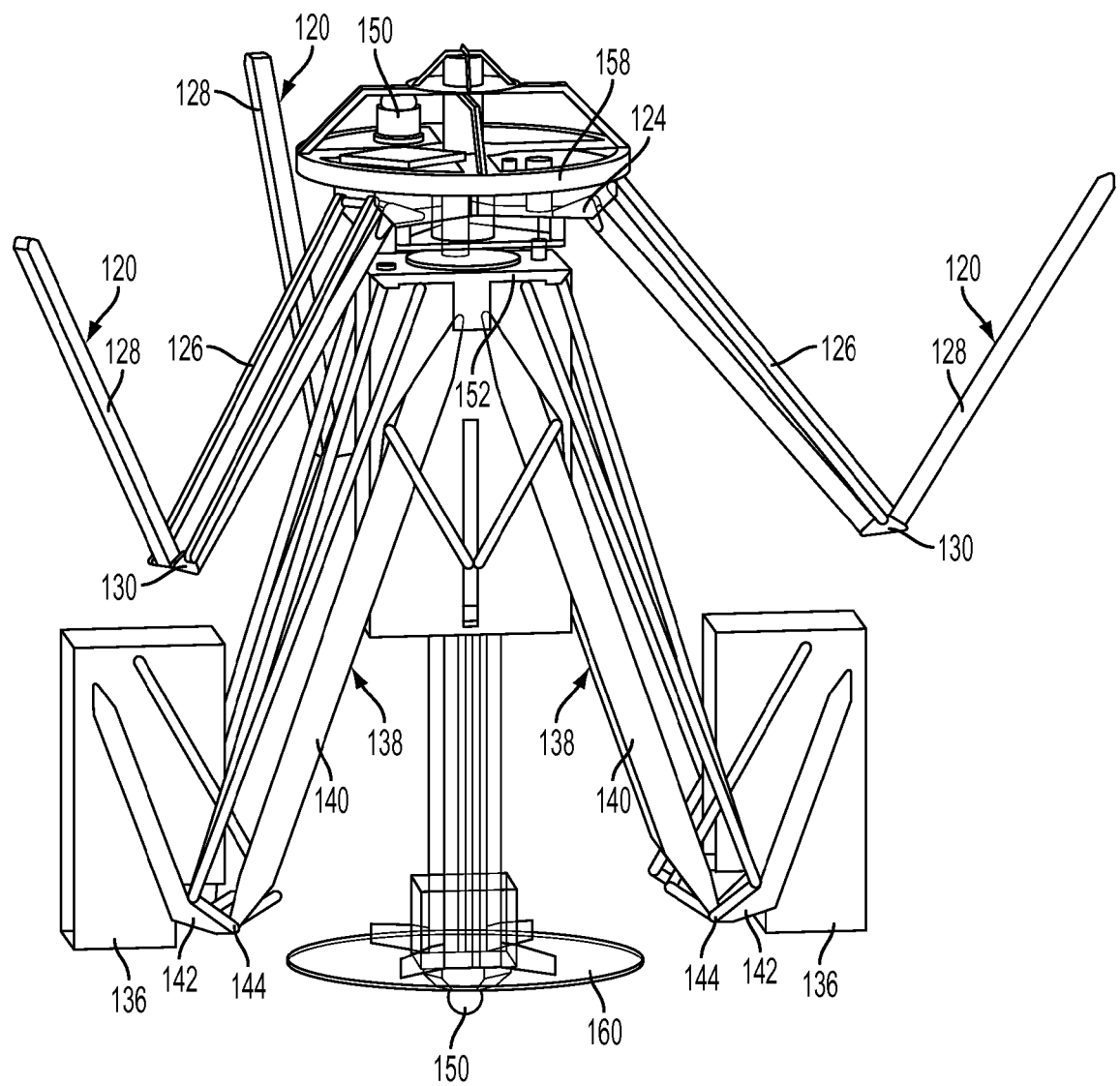
FIG. 5 illustrates another view of an apparatus capable of providing remote access to a structure, shown in an expanded configuration.
Figure 7:
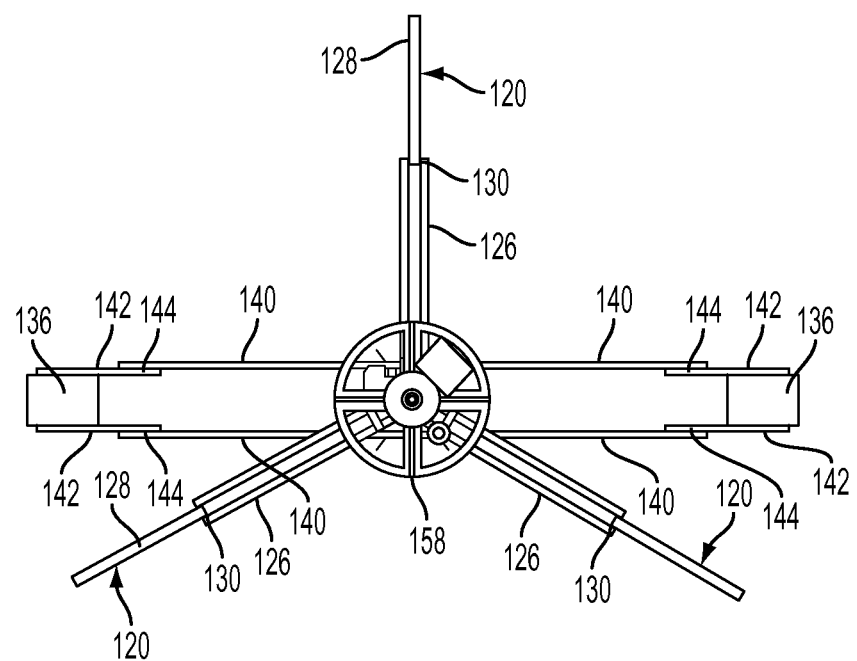
FIG. 7 illustrates another view of an apparatus capable of providing remote access to a structure, shown in an expanded configuration from above.

As shown in FIG. 2, as apparatus 100 is lowered into structure 104 in the collapsed configuration, enclosure 112 remains in position over opening 102. After apparatus 100 is lowered to the desired height in structure 104, apparatus 100 can move into the expanded configuration. As shown in FIG. 3, in the expanded configuration a plurality of stabilizing members 120 are moved radially outward to engage with a surface of the inner wall 122 of structure 104. The number of stabilizing members 120 can vary; however, as best shown in FIGS. 5 and 7, apparatus 100 preferably has three stabilizing members 120 that extend radially from a support body 124 of apparatus 100. Each of the stabilizing members 120 have a first end coupled to the body of the apparatus (e.g., support body 124) and a second end that is configured to contact and engage with a surface of the inner wall 122 of structure 104. When three stabilizing members are provided, the second ends contact the inner wall 122 in a generally triangular pattern (FIG. 7). This generally centers the support body 124 in the structure 104.

The spacing of stabilizing members 120 can also vary. As shown in FIG. 7, stabilizing members 120 can be radially spaced apart from one another by a generally equal amount. Thus, for example, if only two stabilizing members 120 are provided they will preferably be spaced apart about 180 degrees (i.e., in a generally opposing configuration). Similarly, if three stabilizing members 120 are provided, they can be spaced apart about 120 degrees as shown, for example, in FIG. 7. However, if there are more than two stabilizing members 120, it is possible to provide sufficient stabilization of apparatus 100 without providing equal spacing of stabilization members 120. Moreover, depending on the configuration of apparatus 100 and the location of other structures thereon or obstructions on the inner wall 122, it may be desirable to provide stabilizing members 120 that are not equally spaced apart.

As noted above, to accommodate structures that have openings 102 with small diameters relative to an interior space (e.g., an interior diameter), stabilizing members 120 are preferably able to collapse to a profile that allows apparatus 100 to pass through opening 102. At the same time, however, stabilizing members 120 must also be able to expand a sufficient amount to engage with the inner wall 122 of structure 104 when in the expanded configuration. Preferably, apparatus 100 is able to collapse to a diameter that is less than about 5 feet, and more preferably less than about 3 feet. Apparatus 100 is also preferably able to expand to a diameter (to contact the interior walls of a structure) that is at least 10 feet, and, more preferably, at least 15 feet in diameter. In some embodiments, the ratio of a diameter of the expanded configuration to the non-expanded configuration is 2:1 or greater. In other embodiments, the ratio of the diameter of the expanded configuration to the non-expanded configuration is 3:1 or greater.

Figure 8:
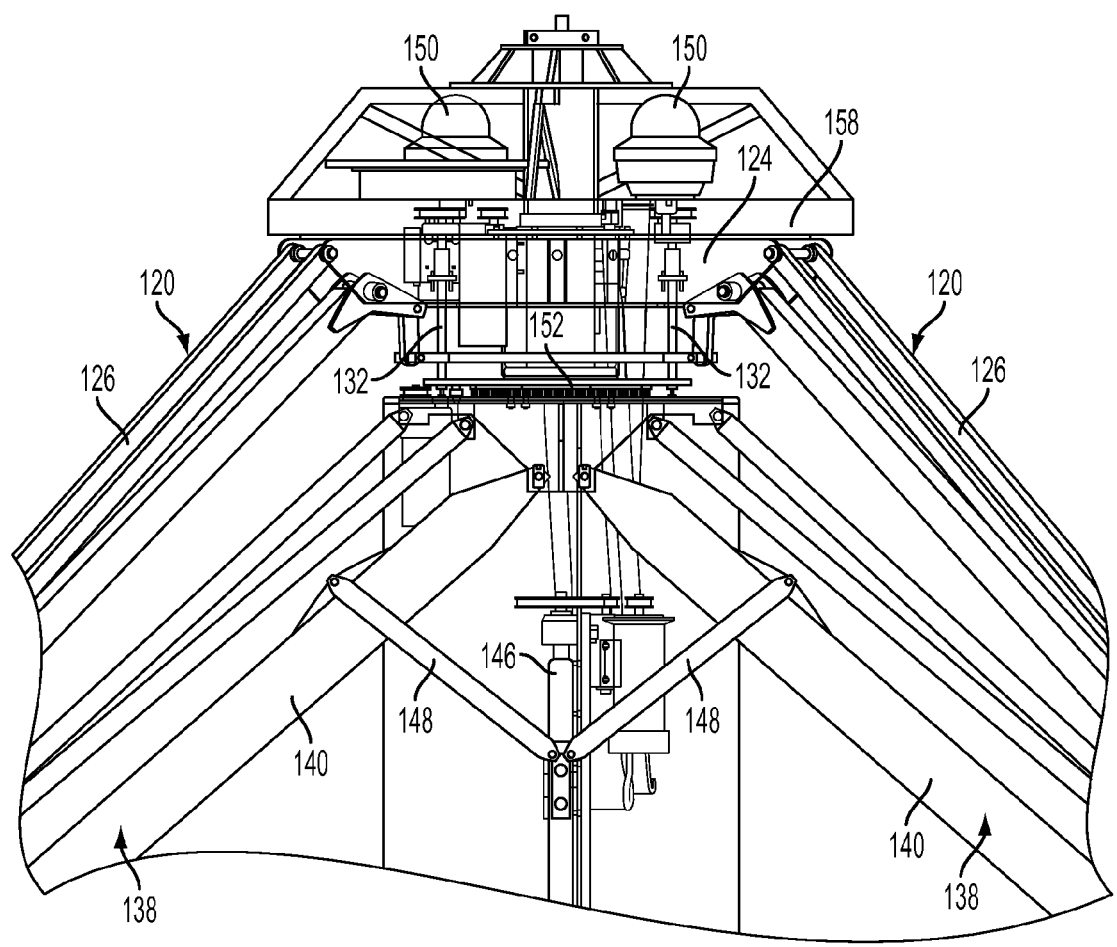
FIG. 8 illustrates a partial view of a top portion of an apparatus capable of providing remote access to a structure.

In some embodiments, stabilizing members 120 can comprise a plurality of arm members linked together. For example, a first arm member 126 can be linked to a second arm member 128 through one or more link members 130. As shown in FIG. 8, actuators 132 can be coupled to each stabilizing arm 120 (e.g., at the first arm members 126) to drive the movement of each stabilizing arm 120 from the collapsed configuration (FIG. 2) to the expanded configuration (FIG. 3). Actuators 132 can comprise one or more linear actuators, such as ball screw actuators.

Figure 4:
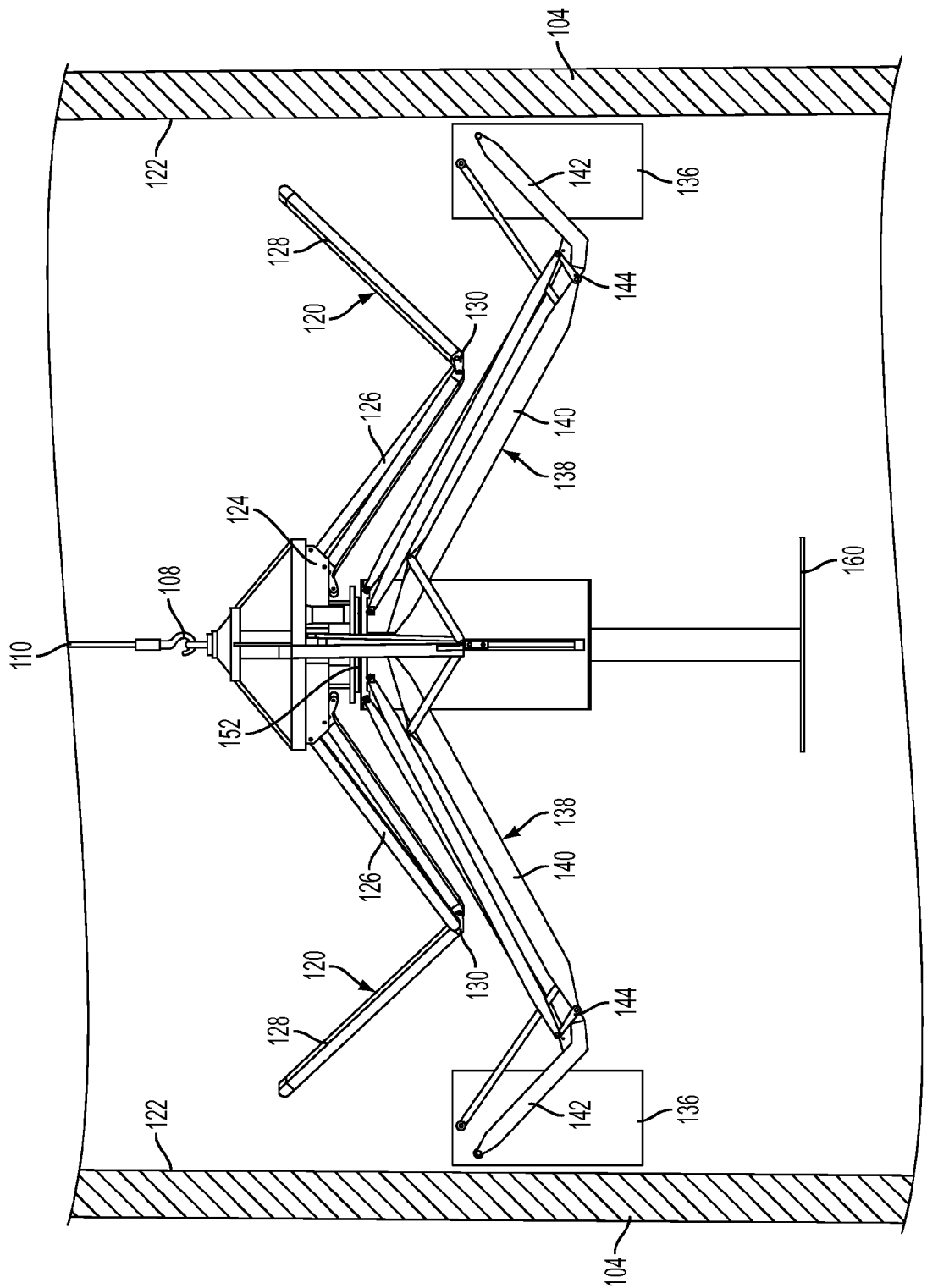
FIG. 4 illustrates another view of an apparatus capable of providing remote access to a structure, shown in an expanded configuration within an off-gas ventilation stack.
Figure 6:
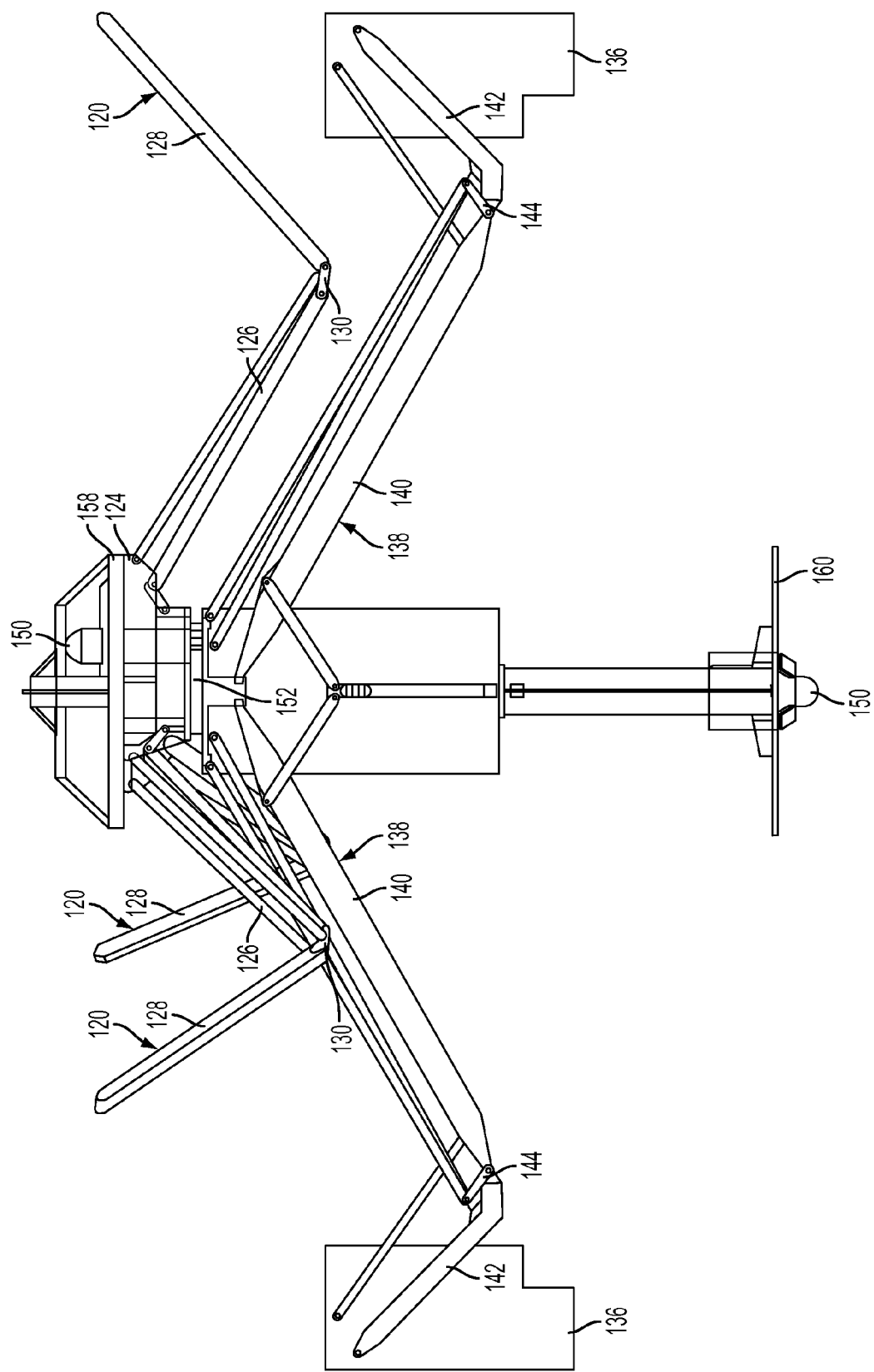
FIG. 6 illustrates another view of an apparatus capable of providing remote access to a structure, shown in an expanded configuration.

By forming stabilizing members 120 with linkages, stabilizing members can expand radially to engage with different sized spaces within a structure. For example, FIG. 3 illustrates apparatus 100 within a structure 104 that has a relatively small inner diameter. In such a situation, the angle between first and second arm members 126, 128 can be relatively small. In order to engage with surfaces within a structure that has a larger inner diameter, however, the angle between first and second arm members 126, 128 can be increased (as shown in FIG. 4) to allow the stabilizing members 120 to contact the surfaces of the larger diameter structure 104. FIGS. 5 and 6 illustrate additional expansion configurations of apparatus 100. For convenience, FIGS. 5 and 6 do not illustrate the structure into which apparatus 100 can be expanded.

In an expanded configuration, stabilizing members 120 engage with the inner wall 122 of structure 104 to generally fix the position of support body 124 relative to the structure 104. Stabilizing members 120 can be configured to engage with the inner wall 122 so that support body 124 is generally centered within the interior of the structure 104. Thus, even if apparatus 100 is delivered off-center into an opening 104 (e.g., by a crane), stabilizing members 120 can adjust the location of apparatus 100 until it is generally centered within the interior of structure 104.

Once stabilizing members 120 are engaged with a surface of structure 104, one or more instrument supports 136 can be moved radially outward towards the surface of inner wall 122. Instrument supports 136 can contain or otherwise carry instruments that are configured to inspect and/or analyze materials or conditions of the structure, or to collect samples of the structure for later analysis.

Instrument supports 136 can be provided on one or more moveable members 138. Moveable members 138 are moveable between a collapsed configuration that allows apparatus 100 to achieve a relatively small profile to pass through opening 102, and an expanded configuration that moves instrument supports 136 adjacent inner wall 122 to perform various acts relating to collection and/or analysis of samples.

Like stabilizing members 120, moveable members 138 can comprise a plurality of arm members or mechanical linkages. For example, moveable members 138 can comprise a first arm member 140 and a second arm member 142 coupled together via one or more link members 144. If additional support is desired, a pair of first arm members 140 and second arm members 142 can be associated with each instrument support 136, such as on opposing sides of instrument support as shown, for example, in FIGS. 7 and 9.

After radially extending stabilizing members 120, instrument supports 136 can be moved adjacent the surface of the inner wall 122 of the structure 104. Depending on the instruments carried by instrument supports 136, instrument supports 136 can be moved very close to the inner wall (and in some circumstances can contact the inner wall) or instruments supports 136 can be spaced apart from the inner wall a greater distance.

Movement of moveable members 138 can be activated similar to movement of stabilizing members 120. For example, as shown in FIG. 8, one or more actuators 146 can be associated with each moveable member 138 to drive moveable members 138 from the collapsed configuration to the expanded configuration. For example, a ball screw actuator can be coupled to one or more first arms 140 via one or more linkage 148 and linear movement of the actuator can cause linkage 148 to cause first arms 140 to move radially outward.

Stabilizing members 120 also provide a platform about which instrument supports 136 can be rotated. Moveable members 138 can be coupled to a base 152 that is rotatable relative to stabilizing members 120. For example, base 152 can be rotatably coupled to support body 124. Thus, when stabilizing members 120 are in the expanded configuration so that stabilizing members 120 and support body 124 are generally fixed relative to structure 104, base member 152 can rotate to alter the position of moveable members 138 and instrument supports 136 within the interior of structure 104. In this manner, instrument supports 136 can be rotated to different locations within the interior of structure 104 to analyze or take samples at different areas of structure 104.

When removing apparatus 100 from structure 104, apparatus 100 can be collapsed back to the non-expanded configuration generally shown in FIG. 2. For example, moveable members 138 can first be moved back into the non-expanded configuration. Then, stabilizing members 120 can be radially collapsed and moved back into the non-expanded configuration, thereby releasing apparatus 100 from the fixed position relative to structure 104. Once in the non-expanded configuration, apparatus 100 can be raised (e.g., by a crane) back into enclosure 112 in the configuration shown in FIG. 1.

As apparatus 100 enters enclosure 112, apparatus 100 can engage with enclosure 112. For example, at the top of apparatus 100, a first engagement member 158 can be provided to engage with a top portion of enclosure 112. Similarly, at the bottom of apparatus 100, a second engagement member 160 can be provided to engage with the containment cap 114. Accordingly, as apparatus moves upward and out of opening 102, first engagement member 158 contacts and engages with a top portion of enclosure 112, while second engagement member 160 contacts and engages with a bottom portion of enclosure 112 (e.g., containment cap 114). In this manner, as apparatus 100 is continued to be raised upwards, enclosure 112 is engaged with apparatus 100 so that enclosure 112 is also removed from structure 104.

Sampling Instruments

Various instruments can be carried by apparatus 100, including on or within instrument supports 136. For example, a plurality of cameras 150 can be provided on apparatus 100 to obtain images of structure 104 from within. As shown in FIG. 3, for example, cameras can be positioned at the top and bottom of apparatus 100 to facilitate remote-controlled delivery of apparatus 100 into and out of structure 104. In addition, cameras 150 can be positioned at various locations along the sides and/or within instrument supports 136 to provide an operator of apparatus 100 with additional information about the interior of structure 104. For example, images obtained from cameras 150 can provide important information about the structural integrity and other conditions of structure 104. To further improve the views obtained by cameras 150, one or more lights can be provided to illuminate portions of the interior of structure 104.

Figure 9:
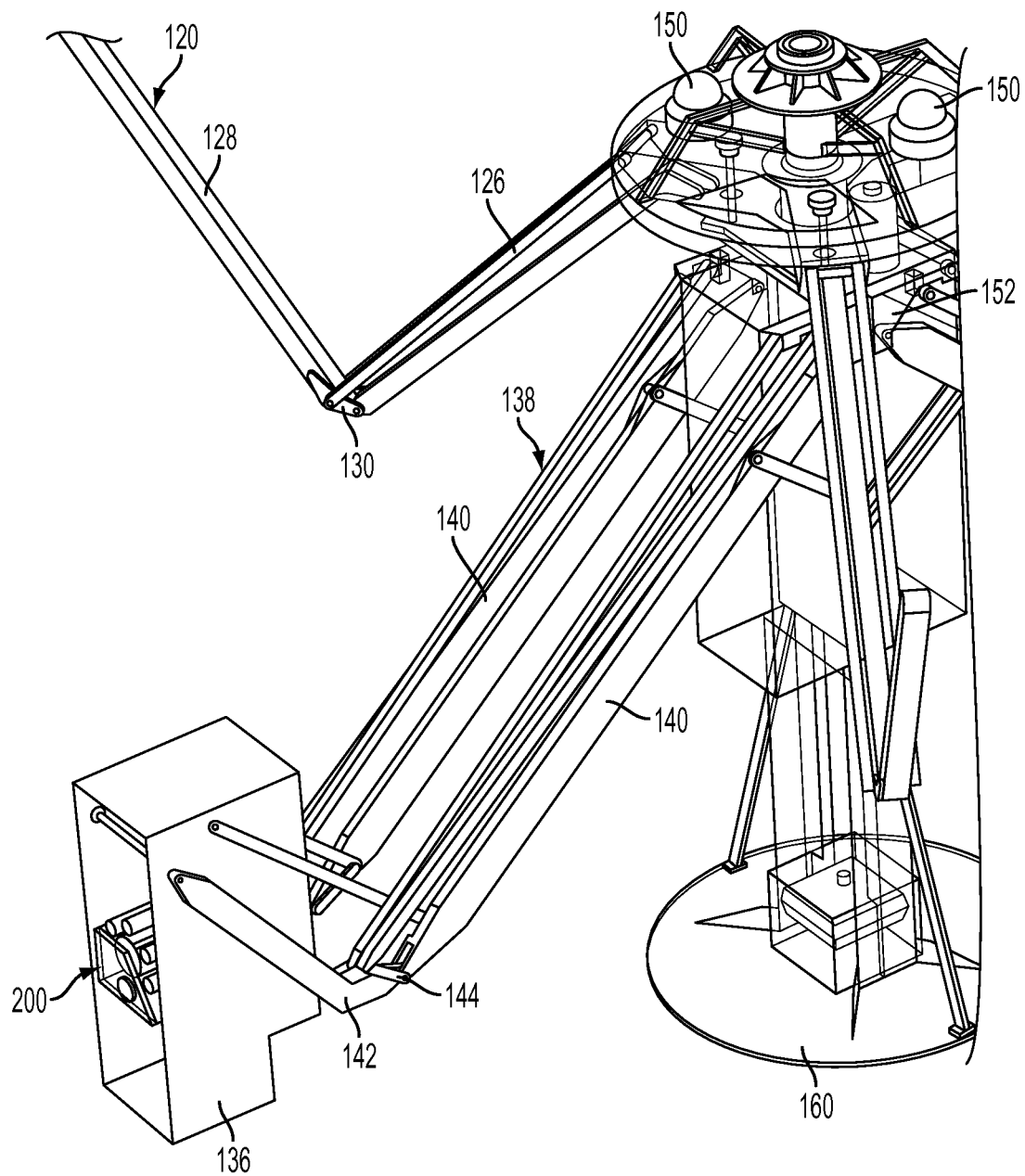
FIG. 9 illustrates a partial view of a side portion of an apparatus capable of providing remote access to a structure, shown with an instrument positioned in an instrument support.
Figure 13:
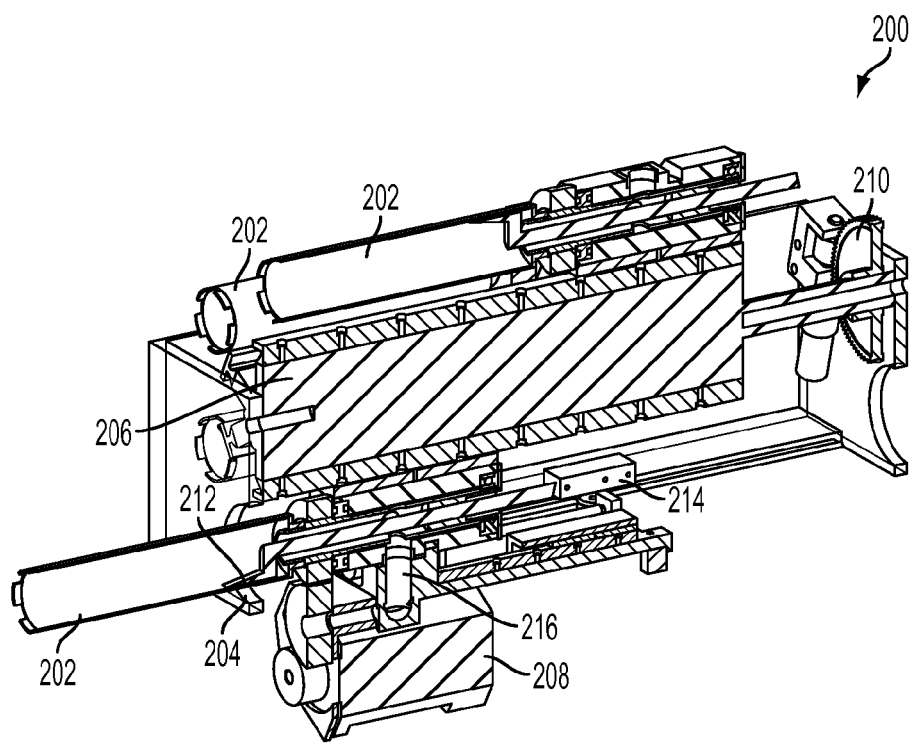
FIG. 13 illustrates a cross-sectional view of the device of FIG. 12.
Figure 14:
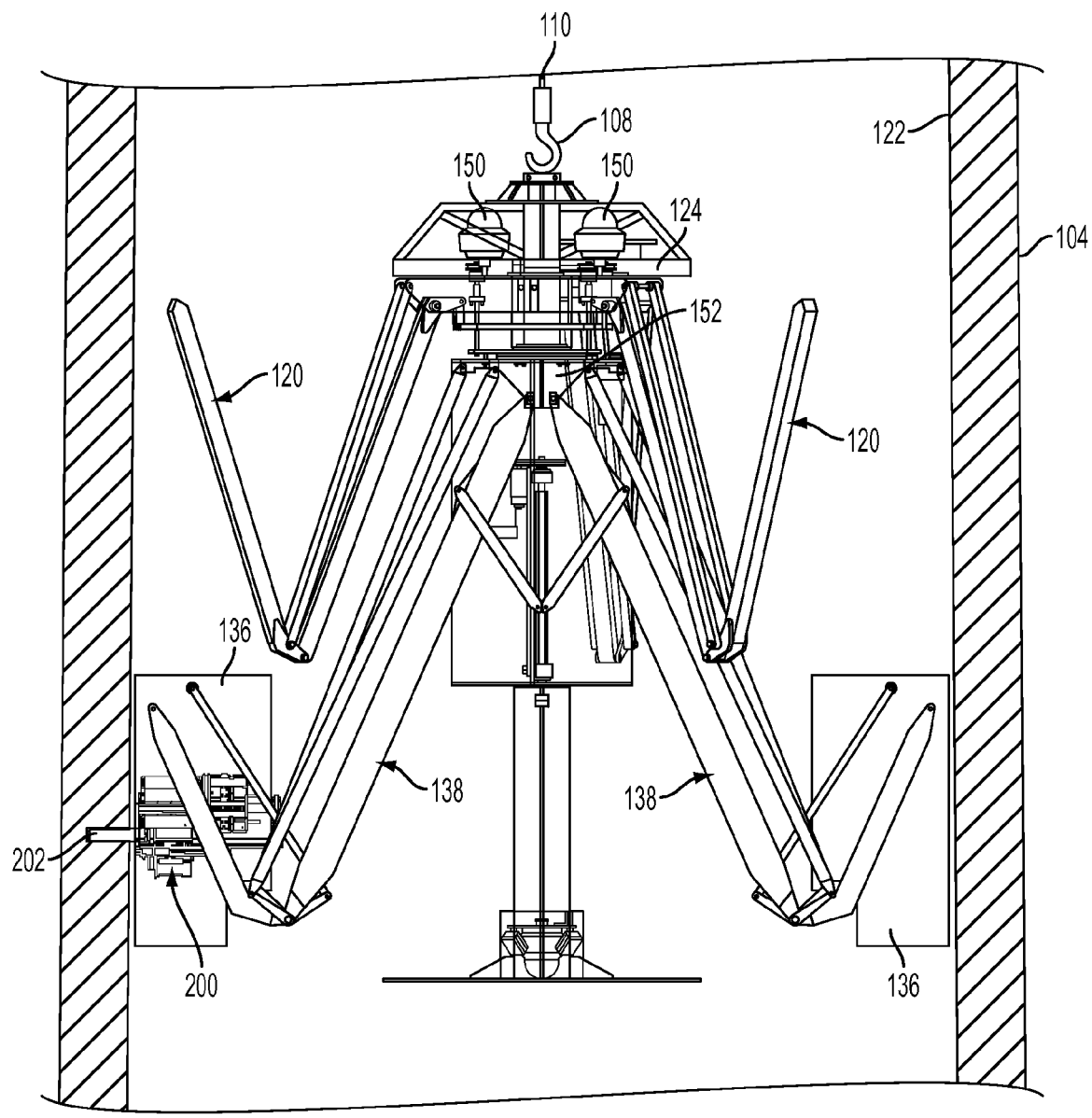
FIG. 14 illustrates a partially transparent view of a sampling apparatus being used in combination with an apparatus capable of providing remote access to a structure, such as the inside of an off-gas ventilation stack.
Figure 15:
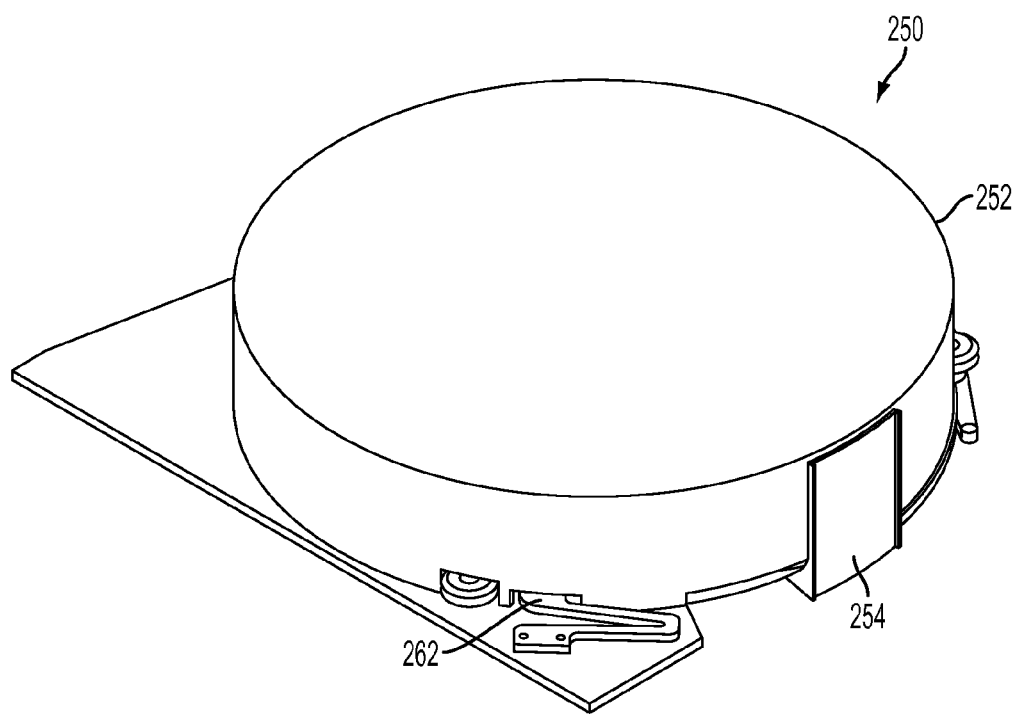
FIG. 15 illustrates a perspective view of a sampling apparatus.

Other instruments can be provided to obtain samples from the inner walls of structure 104. FIGS. 9-14 illustrate embodiments of a sampling apparatus 200. Sampling apparatus 200 can be carried by instrument support 136 as shown in FIGS. 9 and 14. Although sampling apparatus 200 is generally shown carried within an exterior-facing bay of instrument support 136, sampling apparatus 200 can be carried by apparatus 100 in other manners and, in some embodiments, can operate independently of apparatus 100.

Figure 10:
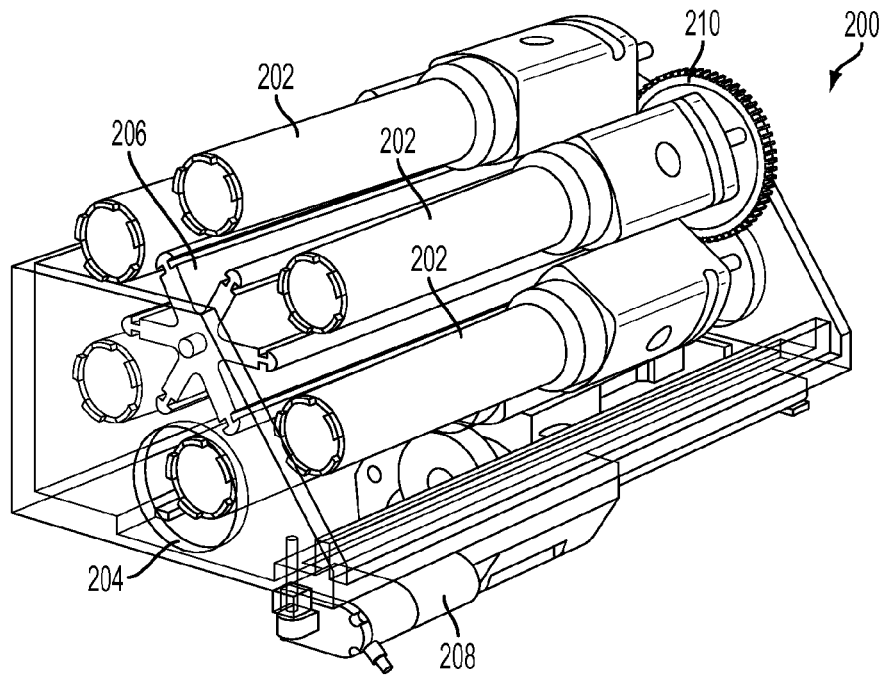
FIG. 10 illustrates a partially transparent, perspective view of a sampling apparatus.
Figure 11:
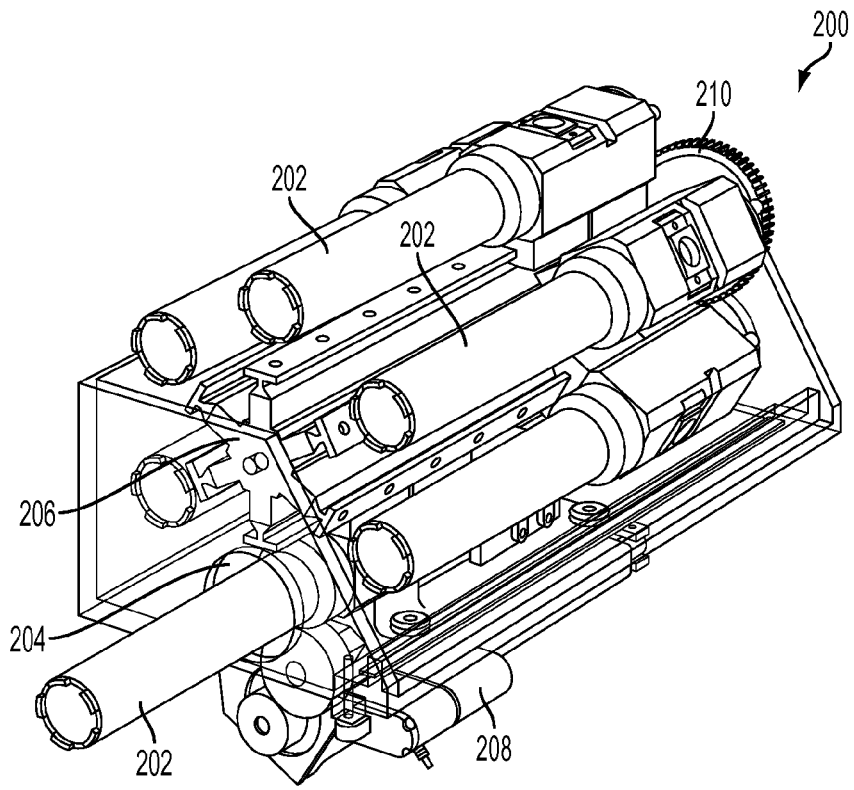
FIG. 11 illustrates a partially transparent, perspective view of a sampling apparatus, shown with a sampling device at least partially extended from the sampling apparatus.
Figure 12:
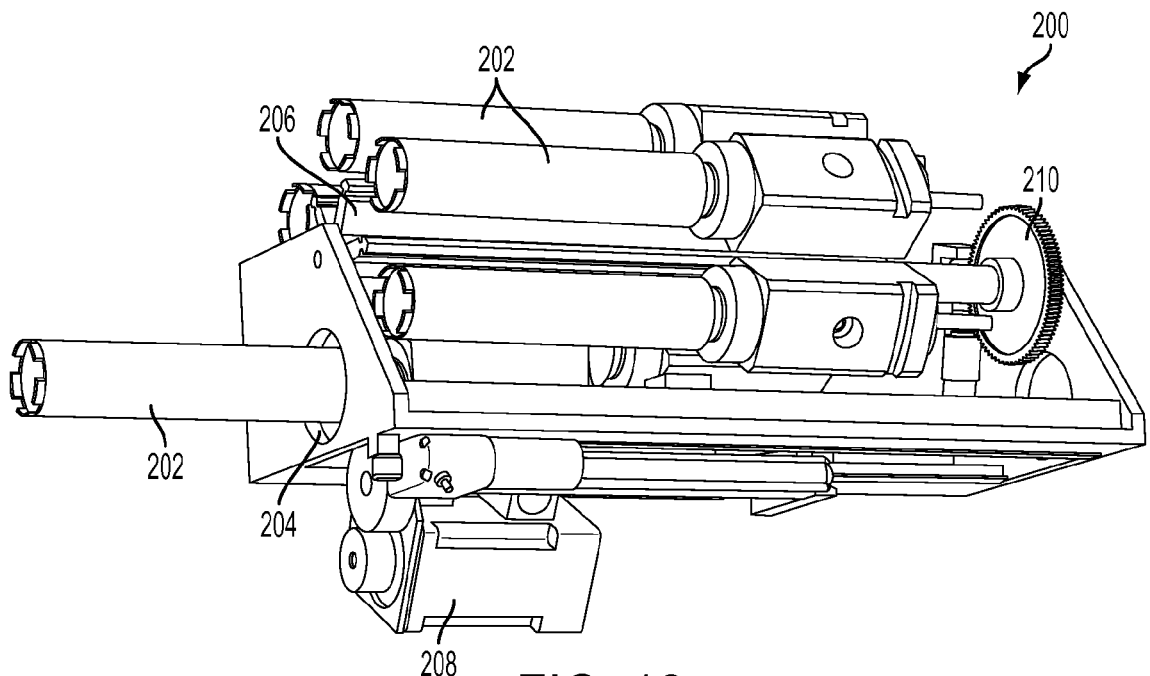
FIG. 12 illustrates another perspective view of a sampling apparatus, shown with a sampling device at least partially extended from the sampling apparatus.

As shown in FIG. 10, sampling apparatus 200 can comprise a core extraction system that is configured to obtain a plurality of core samples from structure 104. A plurality of core bits 202 are arranged on a rotatable turret 206 to allow each core bit 202 to be rotated into a deployment position. For example, one or more openings or windows 204 can be provided in sampling apparatus 200 through which a core bit 202 can be extended to obtain a sample from structure 104. Thus, in operation, when a core bit is aligned with opening 204 (e.g., FIG. 10), the core bit can be moved through opening 204 (e.g., FIG. 11), and a core bit drive motor 208 can cause core bit 202 to rotate and cut into inner wall 122. After core bit 202 has completed its coring action and captured a sample within core 202, core bit 202 can be retracted back through opening 204.

To obtain another sample, sampling apparatus 200 can be moved within the structure to a new location. The movement of sampling apparatus 200 to a new location can be achieved by, for example, rotating base member 152 relative to support body 124 to alter the location of moveable members 138 and instrument supports 136 carried thereon.

To obtain another sample with a different core bit 202, a turret drive 210 can be provided to rotate the turret 206 to align a new core bit 202 with opening 204. New core bit 202 can then be driven by core bit motor 208 and a new sample can be obtained and captured within the new core bit 202.

After core bit 202 has drilled into structure 104 a desired amount, the sample will be captured within core bit 202. However, the portion of the sample near the drilling end of core bit 202 may remain attached to structure 104. Accordingly, to facilitate sample removal, a force is desirably applied to the sample in a direction generally perpendicular to the axis of the sample itself. FIG. 13 illustrates a tool 212 that can be wedged into the interior of the core bit to facilitate the separation of the sample from the structure. Tool 212 can comprise a ramped portion that can be pushed along a portion of the sample to cause it to break off from structure 104 after the core bit 202 has drilled to the desired depth. A hammer tool 214 or other such mechanism can be provided to exert a force in the general direction of the axis of core bit 202 to cause tool 212 to move into core bit 202 until the ramped portion causes the sample to break off from structure 104.

As shown in FIG. 13, a vacuum port 216 can also be provided to draw a vacuum (i.e., produce a negative pressure area) through and/or around the core bit 202 to help remove dust and other debris that is generated by the cutting action. The negative pressure provided by vacuum port 216 can also help extract the core sample after the sample is separated from structure 104.

Thus, in operation, apparatus 100 can be delivered into structure 104 and stabilizing members 120 can center and hold apparatus 100 within the structure. An instrument support 136 can be radially extended until it is adjacent the inner wall 122 of structure 104. As shown in FIG. 14, once instrument support 136 is in the desired position adjacent inner wall 122, a core bit 202 can be aligned with an opening 204 and core bit motor 208 can engage a bit drive gear to cause core bit 202 to advance and engage with a surface of structure 104. Once core bit 202 reaches the desired depth and the sample is captured within core bit 202, core bit 202 can be retracted back into sampling apparatus 200. After the core bit 202 and sample are retracted into sampling apparatus 200, turret 206 can be rotated to present a new core bit 202 for deployment into structure 104. Collected samples can remain within the core bits 202 of sampling apparatus 200 until apparatus 100 is removed from structure 104. Once apparatus 100 is removed from structure 104, personnel can access the collected samples and remove them from core bits 202 for analysis.

Thus, a plurality of core samples can be captured by sampling apparatus 200. Although six core bits 202 are illustrated in FIGS. 9-14, it should be understood that sampling apparatus 200 can be modified to have more or fewer core bits 202. In some embodiments, at least three core samples can be captured by sampling apparatus 200. In other embodiments, at least six samples can be captured by sampling apparatus 200. In yet other embodiments, multiple samples are collected and stacked inside a single core bit 202.

In some embodiments, the torque-feedback control of the advance speed of a core bit 202 can be automated. Thus, to prevent jamming of core bits 202 when cutting into the structure, an advancing mechanism can be configured to stop advancing core bit 202 when a pre-set amount of force is reached and to continue advancing core bit 202 when the determined amount of force is below the pre-set amount. In addition, an automated break-away for each core bit 202 can be provided in case a core bit 202 because jammed or stuck within structure 104.

FIGS. 15-18 illustrate another sampling apparatus 250 that is configured to capture a plurality of samples from structure 104. Sampling apparatus 250 is configured to capture samples from structure 104 by moving a sampling surface into contact with the surface of inner wall 122. Sampling apparatus 250 can also be carried by instrument support 136 in the same manner as shown in FIGS. 9 and 14. Sampling apparatus 250 can also be carried by apparatus 100 in other manners and, in some embodiments, can operate independently of apparatus 100.

Figure 16:
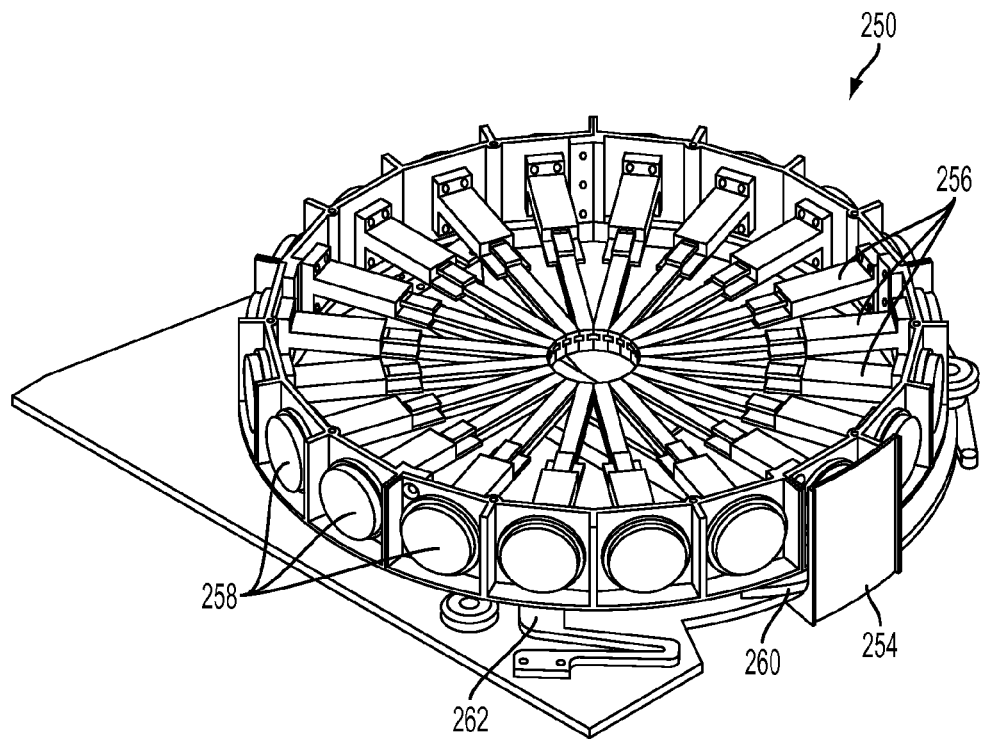
FIG. 16 illustrates a perspective view of a sampling apparatus that comprises a plurality of sampling surfaces, shown with a cover removed.
Figure 17:
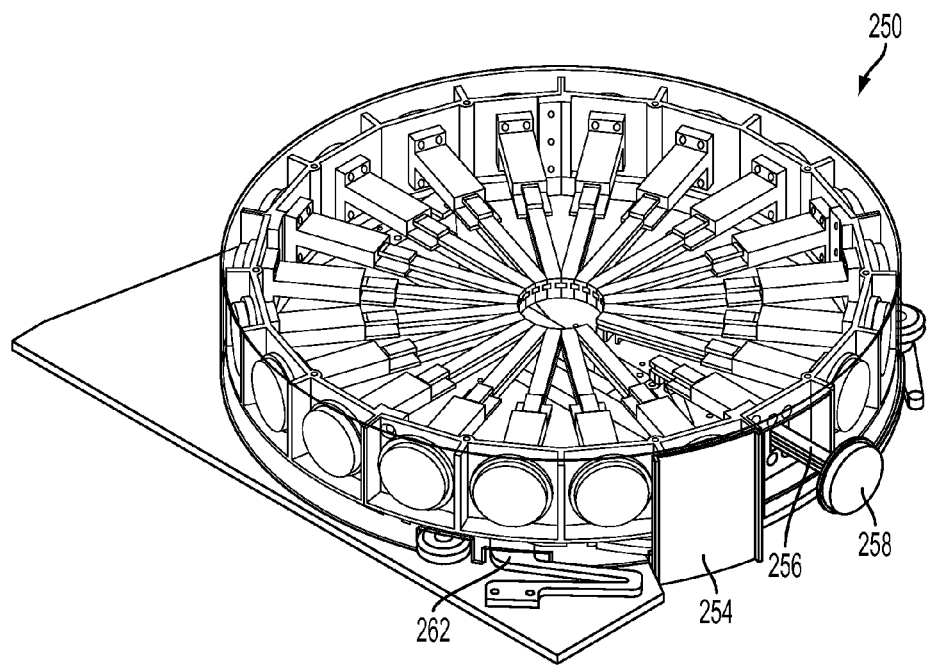
FIG. 17 illustrates another perspective view of a sampling apparatus that comprises a plurality of sampling surfaces, shown with a cover removed and with a sampling surface extended to obtain a sample.

As shown in FIGS. 15-18, sampling apparatus 250 comprises a cover 252 with a shutter 254 that is movable between a closed position (FIG. 15) and an open position (FIG. 17). A plurality of sampling surfaces 258 are provided within cover 252. Each sampling surface 258 is coupled to an arm or plunger 256. Sampling surfaces 258 can be any surface capable of obtaining and retaining a sample of the surface of inner wall 122 upon contact. For example, sampling surfaces 258 can comprise adhesive pads that can capture a portion of the wall surface when the sampling surface 258 contacts the wall surface.

Figure 18:
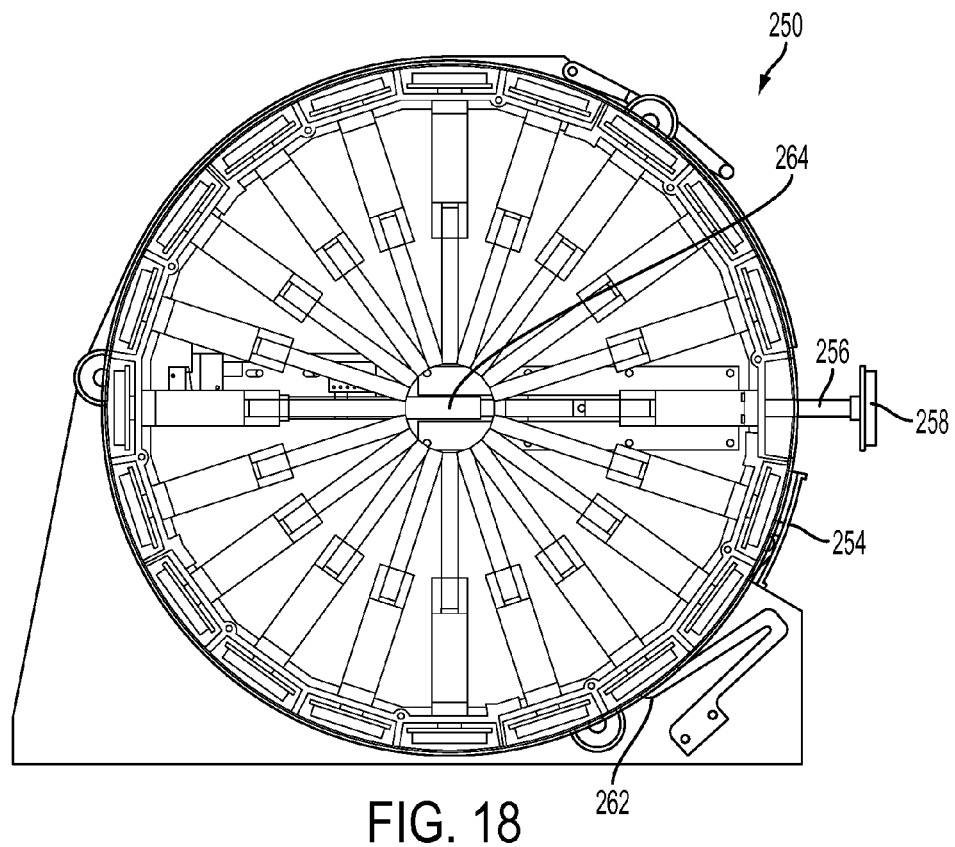
FIG. 18 illustrates another perspective view of a sampling apparatus that comprises a plurality of sampling surfaces, shown with a cover removed and with a sampling surface extended to obtain a sample.

As shown in FIG. 16-18, sampling surfaces 258 can be arranged radially around the outer edge of a carousel tray. In operation, sampling apparatus 250 can be positioned adjacent the surface of the inner wall 122 and shutter 254 can open (FIG. 17) to allow a sampling surface 258 to access the surface of the inner wall 122. Arm 256, with a sampling surface 258 positioned at one end, can be extended until the sampling surface 258 contacts the surface of the inner wall 122. Upon contact with the surface of the inner wall 122, a portion of the surface of the inner wall 122 can be captured on sampling surface 258 for later inspection and/or analysis. After capturing the sample, arm 256 and sampling surface 258 can be retracted back into sampling apparatus 250, and shutter 254 can close.

Additional samples can be captured by rotating the carousel and advancing a new arm 256 and sampling surface 258 into alignment with the opening associated with shutter 254. To capture the next sample, shutter 254 can open again and the new arm 256 and sampling surface 258 can extend outward to capture the next sample. In this manner, a plurality of samples can be captured by sampling apparatus 250. Also, because the carousel is substantially enclosed by cover 252 and shutter 254 except when a sample is captured through the open shutter 254, the captured samples are generally protected from cross contamination and the environment within the structure.

Sampling apparatus 250 can be configured so that it can be operated using only two actuation devices. The first actuation device is configured to open shutter 254 and index the carousel 1/x, with x being the number of arms 256 and sampling surfaces 258. Thus, for example, if there are twenty sampling surfaces, the carousel can be advanced 1/20 of a turn each time shutter 254 opens. First actuation device can comprise any actuator that can rotate the carousel. If desired, an index detent 262 and an index pawl 260 can be provided to allow the carousel to move only the desired amount necessary to move an arm 256 and sampling surface 258 that have been deployed away from the opening associated with shutter 254 and deliver the next arm 256 and sampling surface 258 into position for deployment.

When shutter 254 moves into the open position (FIG. 17), the second actuation device 264 is configured to extend an arm 256 through an opening provided by the movement of shutter 254. Second actuation device 264 can comprise any actuator capable of exerting a force sufficient to radially extend arm 256. If desired, a force sensing and limiting mechanism can be provided to limit the amount of force exerted by arm 256 on the surface of inner wall 122. For example, in some embodiments, the force sensing and limiting mechanism can be configured to limit pressure exerted by the sampling surface 258 on the target area to about 3 lbs. or less.

In some embodiments, break-away mechanisms can be provided on (or near) arms 256 to allow at least portions of aims 256 and sampling surfaces 258 to break off from the carousel if the sampling surface 258 becomes unintentionally attached to the surface of the inner wall 122. The break-away mechanism can comprise shear pins, detents or the like provided along arms 256. Such detents can also be beneficial to facilitate removal of the samples (and sampling surfaces 258) from arms 256 for inspection and analysis.

Once sampling apparatus 250 has completed gathering samples, the carousel and captured samples can be easily removed and replace as a unit. In some embodiments, the removal and replacement of the carousel can be effected by releasing a spring-loaded roller and lifting the carousel out from apparatus 250. Second actuation device 264 can be separate from the removable carousel and therefore, replacement of the carousel does not require replacement of second actuation device 264.

The instruments described herein can be carried in various manners and combinations by apparatus 100. For example, two instrument supports 136 can be provided with one instrument support 136 carrying a sampling apparatus 200 and another carrying a sampling apparatus 250. Additionally, other instruments, such as cameras 150 and radiation detectors, as discussed below, can be provided in one or more instrument supports 136 or otherwise carried by apparatus 100.

Figure 19:
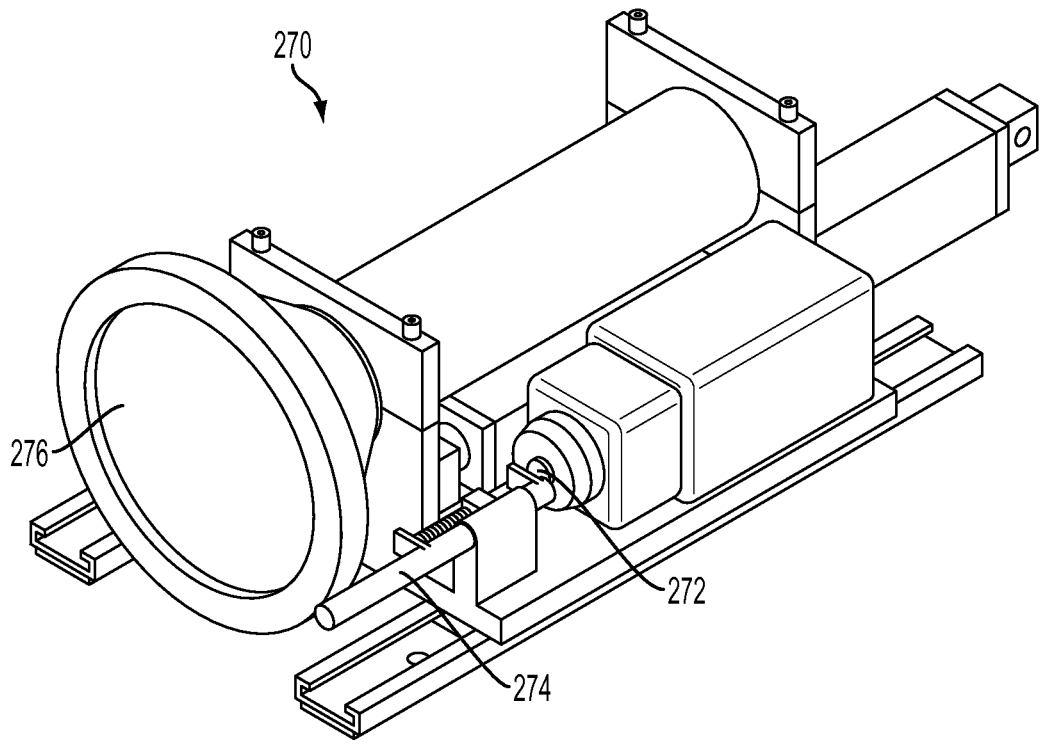
FIG. 19 illustrates a device for detecting radiation that can be delivered into a structure on an instrument support.
Figure 20:
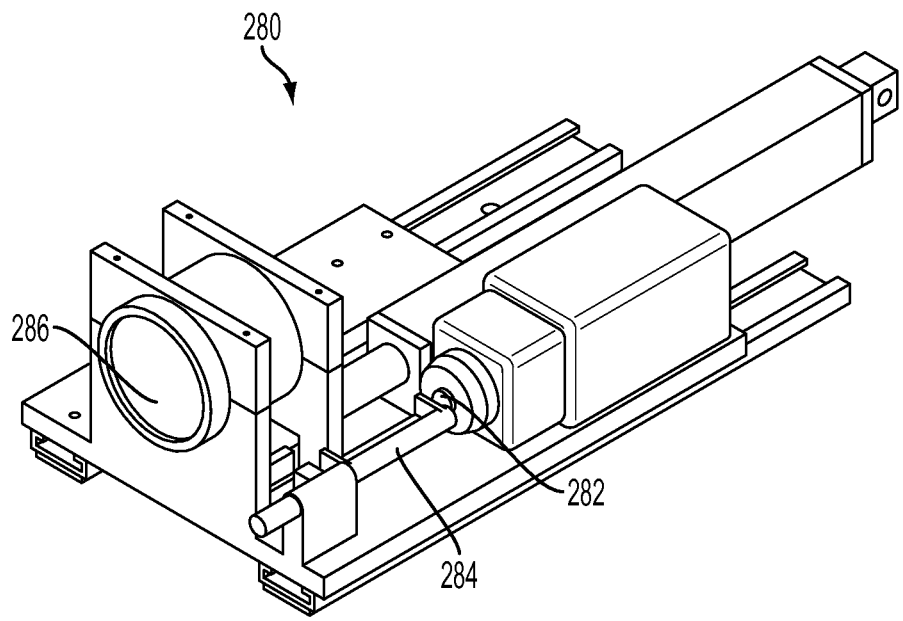
FIG. 20 illustrates another device for detecting radiation that can be delivered into a structure on an instrument support.

FIGS. 19 and 20 illustrate other instruments that can be delivered by apparatus 100 into structure 104. FIG. 19 illustrates a radiation detector 270 that is configured to detect gamma radiation, while FIG. 19 illustrates a radiation detector 280 that is configured to detect alpha radiation. Although only gamma and alpha detectors are described above, it should be understood that other radiation detectors can be used in connection with apparatus 100.

For radiation detection, it can be useful to position a sensor less than 1 inch from a surface and, in some circumstances, less than ¼ inch from the surface. To achieve this, both detectors can comprise a motion limiting member 274, 284 so that detectors 270, 280 can be positioned the desired distance away from the surface of the inner wall 122 during the sampling period. Motion limiting members 274, 284 can be positioned adjacent a switch (272, 282 respectively) that activates a sensor (276, 286 respectively). When motion limiting members 274, 284 contact the surface of the wall, motion limiting members can move until they contact their respective switch 272, 282, at which time the distance between the sensor 276, 286 is fixed and the sensor 276, 286 is activated.

Apparatus 100 is preferably powered by batteries carried on apparatus 100. The batteries can be carried, for example, on a surface of engagement member 160. However, it should be understood that the number, size, and type of batteries carried by the apparatus 100 can vary, so long as the batteries provide sufficient power to the apparatus and do not substantially interfere with the operation of the various features described herein.

Apparatus 100 can be remotely controlled through a wired or wireless network for example. Instructions from the operator can be received on the apparatus 100 via an on-board command system. Thus, a remote operator can control the expansion and collapsing of the stabilizing members, the moveable members, and the activation of the sampling systems. The remote operator can also observe the structure 104 and apparatus 100 via on-board cameras that are configured to deliver video signals to the location of the operator.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims. This technology is available for license in certain fields of use by the assignee of record.

We claim:

1. An apparatus for providing remote access to a structure, the apparatus comprising:
   a support member;
   at least one stabilizing member having a first portion coupled to the support member and a second portion configured to engage with the structure to restrict relative movement between the support member and the structure, the at least one stabilizing member being radially expandable from a first configuration where the second portion does not engage with a surface of the structure to a second configuration where the second portion engages with the surface of the structure; and
   at least one moveable member having a first end and a second end, the first end being coupled to the support member and the second end being coupled to an instrument, the moveable member being configured to radially expand to move the instrument adjacent to a surface of the structure,
   wherein the instrument comprises a plurality of core bits rotatably coupled to a turret and at least one driver configured to advance each of the core bits towards the surface of the structure and rotate the core bits to capture samples from the structure.

2. The apparatus of claim 1, wherein the at least one stabilizing member comprises three stabilizing members that extend from the support member, and the second portions of the stabilizing members contacting the surface of the structure in a generally triangular pattern.

3. The apparatus of claim 2, wherein the three stabilizing members each comprise a first arm member, a second arm member, and a link member pivotably coupling the first and second arm members.

4. The apparatus of claim 1, further comprising a base member that is coupled to the support member and the first end of the at least one moveable member, the base member being rotatable relative to the support member.

5. The apparatus of claim 1, wherein the at least one moveable member comprises a first arm member, a second arm member, and a link member pivotably coupling the first and second arm members.

6. The apparatus of claim 5, wherein the instrument is carried by an instrument support coupled to the second end of the at least one moveable member.

7. The apparatus of claim 1, wherein the instrument comprises:
   a housing that substantially encloses the plurality of core bits, the housing having at least one opening through which each core bit can be advanced toward the surface of the structure; and
   a vacuum port positioned generally in line with the opening to capture debris from the vicinity of a rotating core bit.

8. The apparatus of claim 7, wherein the instrument comprises:
   a tool having a ramped portion that is moveable at least partly into an interior area of the core bits after a sample has been captured to separate the captured sample from the structure.

9. The apparatus of claim 1, wherein the instrument comprises:
   a plurality of extension members having a first end and a second end, the second end of the extension members having a sampling surface; and
   a housing that substantially encloses the plurality of extension members, the housing having at least one opening through which each extension member can be advanced towards the surface of the structure,
   wherein the sampling surfaces are configured to contact the surface of the structure to obtain a sample of the surface of the structure.

10. The apparatus of claim 9, wherein there is a single opening in the housing through which each of the extension members is advanced, and the plurality of extension members are rotatable so that each extension member can be moved into alignment with the single opening.

11. The apparatus of claim 10, further comprising a shutter that is movable between a closed position where the shutter substantially blocks the single opening and an open position where the shutter does not block the single opening.

12. The apparatus of claim 9, wherein each extension member comprises a detent configured to allow at least a portion of the extension member to break off when a torque is applied to the extension member.

13. The apparatus of claim 1, wherein the instrument comprises a radiation detector.

14. The apparatus of claim 13, wherein the radiation detector comprises a radiation sensor and a motion-limiting member to position the radiation sensor a desired distance from the surface of the structure.

15. The apparatus of claim 1, further comprising:
   a base configured to engage with an opening into the structure; and
   an enclosure extending from the base to generally surround the apparatus as it is removed from the structure.

* * * * *